(12) United States Patent
Ertel et al.

(10) Patent No.: US 6,842,286 B2
(45) Date of Patent: Jan. 11, 2005

(54) OPTICAL SYSTEM AND METHODS THAT COMPENSATE FOR CHANGES IN ATMOSPHERIC CONDITIONS

(75) Inventors: John Phillip Ertel, Portola Valley, CA (US); William Richard Trutna, Jr., Atherton, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 42 days.

(21) Appl. No.: 10/233,940

(22) Filed: Sep. 3, 2002

(65) Prior Publication Data

US 2004/0042079 A1 Mar. 4, 2004

(51) Int. Cl.[7] .......................... G02B 7/00; G02B 27/44; G01J 3/18; H04J 14/02
(52) U.S. Cl. ...................... 359/566; 359/900; 356/305; 356/328; 356/334; 398/84; 398/87; 250/237 G
(58) Field of Search ............................... 359/554, 566, 359/570, 571, 900; 250/237 G; 356/300, 305, 326, 328, 334; 398/48, 84, 87

(56) References Cited

U.S. PATENT DOCUMENTS

| | | | | |
|---|---|---|---|---|
| 4,643,577 A | * | 2/1987 | Roth et al. ................... 356/498 |
| 5,701,320 A | * | 12/1997 | Sugiyama et al. ............. 372/32 |
| 6,134,359 A | * | 10/2000 | Keyworth et al. ............. 385/33 |
| 6,455,842 B1 | * | 9/2002 | Pouteau et al. ........ 250/227.18 |
| 6,529,531 B1 | * | 3/2003 | Everage et al. ................ 372/20 |
| 6,545,826 B2 | * | 4/2003 | Horwitz et al. .............. 359/820 |
| 6,570,652 B1 | * | 5/2003 | Cappiello .................... 356/328 |
| 2004/0017971 A1 | * | 1/2004 | Johannessen ................. 385/37 |

FOREIGN PATENT DOCUMENTS

| | | | |
|---|---|---|---|
| JP | 55-151830 A | * | 11/1980 |
| JP | 58-009119 A | * | 1/1983 |
| JP | 06-311850 A | * | 12/1994 |

* cited by examiner

*Primary Examiner*—John Juba, Jr.

(57) ABSTRACT

Optical systems are provided. One such optical system includes an optical source that propagates a source beam of light. A diffracting component is optically coupled to the optical source and is operative to receive the source beam and produce a diffracted beam. A target is located to receive the diffracted beam. Additionally, a compensating system repositions at least one of the optical source, the diffracting component, and the target in response to a detected change in refractive index of a medium through which the diffracted beam propagates so that the diffracted beam continues to be received by the target. Methods and other systems also are provided.

13 Claims, 3 Drawing Sheets

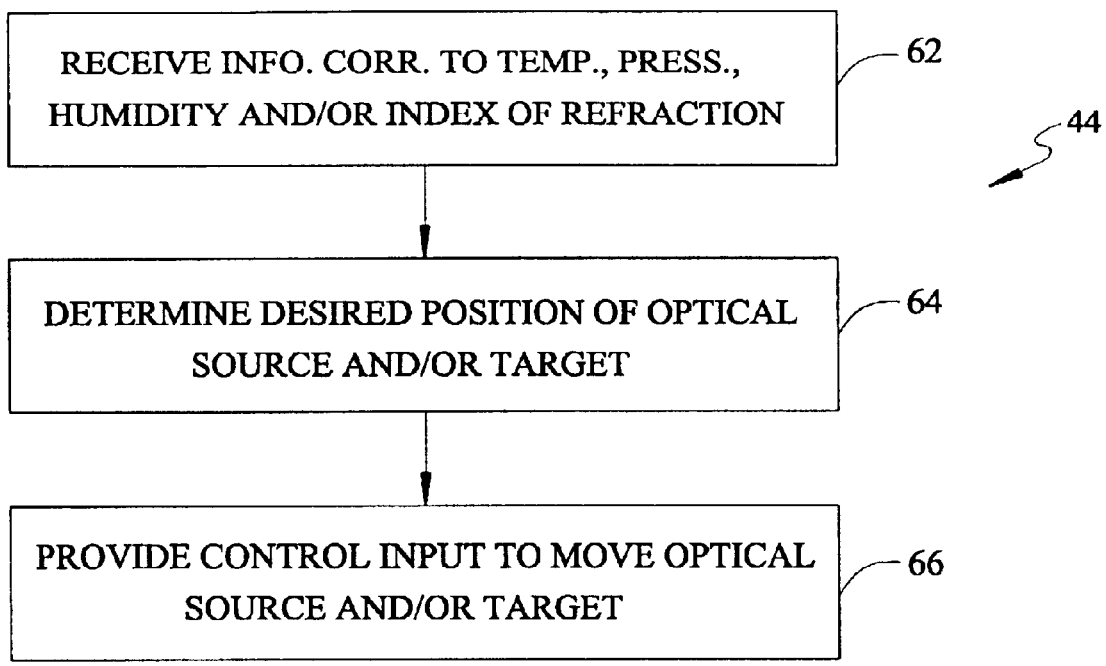
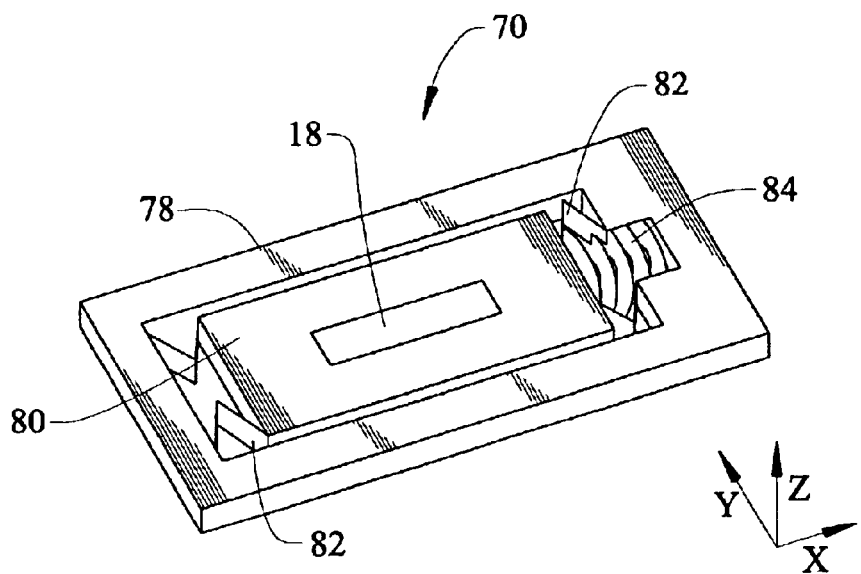

OPTICAL SYSTEM AND METHODS THAT COMPENSATE FOR CHANGES IN ATMOSPHERIC CONDITIONS

FIELD OF THE INVENTION

The present invention is generally related to optical instruments and, more particularly, is related to systems and methods for compensating for changes in the index of refraction of a propagation medium caused by variations in atmospheric conditions on such optical instruments.

DESCRIPTION OF THE RELATED ART

Many optical systems, such as grating-based spectrum analyzers, use diffraction to separate individual wavelengths of light. As is known, with respect to light of a given frequency, the wavelength of the light depends upon the index of refraction of the medium through which the light propagates. If the medium is air, for example, the index of refraction depends upon such factors as barometric pressure, temperature, and humidity.

As is also known, a conventional grating-based spectrum analyzer is not able to distinguish between a change of light caused by a frequency change of the light and a change caused by a refractive index change of the medium though which the light is propagating. Thus, a change in refractive index of air in a spectrum analyzer is an equivalent to a frequency detuning of the spectrum analyzer.

Previous attempts to solve the problem of frequency detuning of spectrum analyzers due to changes in atmospheric conditions typically have not been completely satisfactory. For instance, in one attempt, a spectrum analyzer is filled with a low refractive index gas, such as helium, and then is hermetically sealed. This gives the spectrum analyzer a relatively fixed internal pressure and enables the analyzer to be relatively unaffected by changes in atmospheric pressure. Such sealed spectrum analyzers, however, tend to be bulky and expensive, and also can develop leaks. These leaks can cause the refractive index of the gas located within the spectrum analyzer to change, thus, detuning the spectrum analyzer.

Based on the foregoing, it should be understood that there is a need for improved systems and methods that address the aforementioned and/or other perceived deficiencies of the prior art.

SUMMARY OF THE INVENTION

The present invention involves compensating for changes in the index of refraction of a medium, through which diffracted optical signals propagate, due to variations in atmospheric conditions. With respect to a spectrometer, which is an exemplary device that can use the invention, a change in the index of refraction of a medium results in a shift in the spectrum of light propagating through the device. This shift is particularly evident as the light diffracts from a diffraction grating or other dispersing element of the spectrometer. The shift in the spectrum, in turn, can affect the accuracy of the spectrometer, thus undesirably rendering the spectrometer dependent upon atmospheric changes.

An optical system in accordance with the invention includes an optical source that propagates a source beam of light. A diffracting component is optically coupled to the optical source. The diffracting component receives the source beam of light and produces a diffracted beam. A target is located to receive the diffracted beam. Additionally, a compensating system repositions at least one of the optical source, the diffracting component and the target in response to a change in refractive index of a medium through which the diffracted beam propagates so that the diffracted beam continues to be received by the target.

A method of compensating for a change in index of refraction of a medium in accordance with the invention includes: receiving a source beam of light; diffracting the source beam to produce a diffracted beam, the diffracted beam being directed through a medium to a target, the medium being subject to a change in index of refraction; and compensating for the change in index of refraction of the medium such that the diffracted beam continues to be received by the target.

Clearly, some embodiments of the invention may exhibit advantages in addition to, or in lieu of, those mentioned above. Additionally, other systems, methods, features, and advantages of the present invention will be or may become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 5 is a flowchart depicting a method of operation of another embodiment of a compensating system in accordance with the invention.

FIG. 6 is a perspective view of another embodiment of a compensating system in accordance with the invention.

DETAILED DESCRIPTION

Systems and methods in accordance with the present invention compensate for changes in atmospheric conditions that, otherwise, may adversely affect the operation of grating-based optical systems. In the description that follows, grating-based optical systems configured as spectrometers will be described. There is, however, no intention to limit the invention to spectrometer configurations. In particular, the teachings of the invention also can be used in many other applications where the refractive index of a medium, through which diffracted light propagates, is potentially subject to changes in atmospheric conditions.

Figure 1:
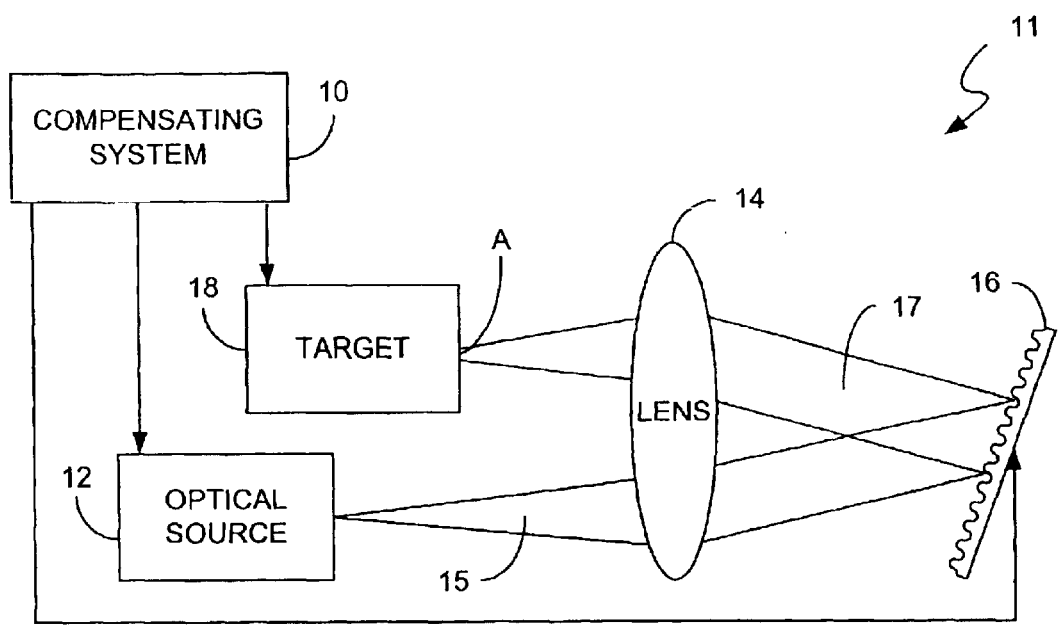
FIG. 1 is a schematic diagram of an embodiment of an optical system in accordance with the present invention.

Referring now to FIG. 1, an embodiment of an optical system 11 in accordance with the invention incorporates an optical source 12 that is optically coupled to a lens 14. A diffracting component 16, e.g., a diffraction grating, is optically coupled to the lens as well as to a target 18. Optical system 11 also includes a compensating system 10 that repositions the optical source 12, the diffracting component 16 and/or the target 18, as will be described in detail later.

In operation, optical source 12 provides a source beam 15 that is collimated by lens 14. The collimated source beam is then directed to and diffracted by diffracting component 16. Diffracting component 16 diffracts the source beam as a diffracted beam 17, and directs the diffracted beam towards the lens. The lens focuses the diffracted beam. Target 18 then receives the focused, diffracted beam.

Figure 2:
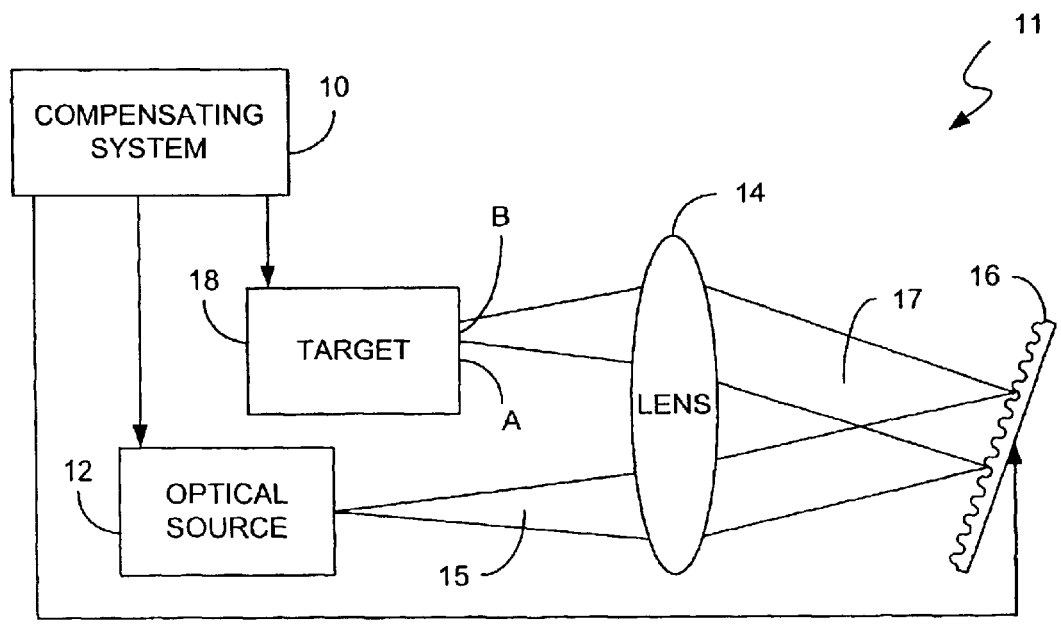
FIG. 2 is a schematic diagram of the optical system of FIG. 1 in which the diffracted beam has been permitted to drift.

Under an initial set of atmospheric conditions, the target 18 receives the diffracted beam at location A. Under another set of atmospheric conditions that change the refractive index of the medium, e.g., air, through which the diffracted beam propagates, the diffraction angle of the diffracted beam is altered. In particular, the diffracted beam arrives at the target at a location B. This is shown in FIG. 2. The diffraction angle of the diffracted beam changes because the change in refractive index of the medium causes the wavelength-dependent wavefronts of the diffracted beam to interact differently with each other, i.e., the change in refractive index alters the angle at which the wavefronts constructively interfere with each other. The change in the index of refraction of the medium can be caused by a change in one or more atmospheric conditions, such as temperature, pressure and humidity. As will be described in detail below, compensating system 10 repositions the optical source, the diffracting component and/or the target in response to such a change in refractive index so that the diffracted beam continues to be received by the target at location A.

Optical source 12 can be one of many different types of sources for providing light. For example, the optical source can be an optical fiber, a laser, e.g., a HeNe laser, a light-emitting diode (LED) or a gas absorption cell illuminated by an LED.

Diffracting component 16 also can be one of many different types. For example, a diffraction grating, a diffractive optical element or other wavelength-dispersing element can be used.

Similarly, target 18 can be one of many different types of optical devices, such as optical detectors and light valves. For example, a liquid crystal (LC) cell, a photodiode or an array of photodiodes can be used. It should be noted that lens 14 is optional and typically is only used when it desired to collimate the source beam and/or focus the diffracted beam.

An embodiment of a method according to the invention will now be described with reference to the flowchart of FIG. 3. It should also be noted that, in some alternative implementations, the functions noted in the various blocks may occur out of order depicted in FIG. 3, or in any other of the accompanying flowcharts. For example, two blocks shown in succession in FIG. 3, may occur substantially concurrently. Alternatively, the functions depicted may occur in reverse order.

Figure 3:
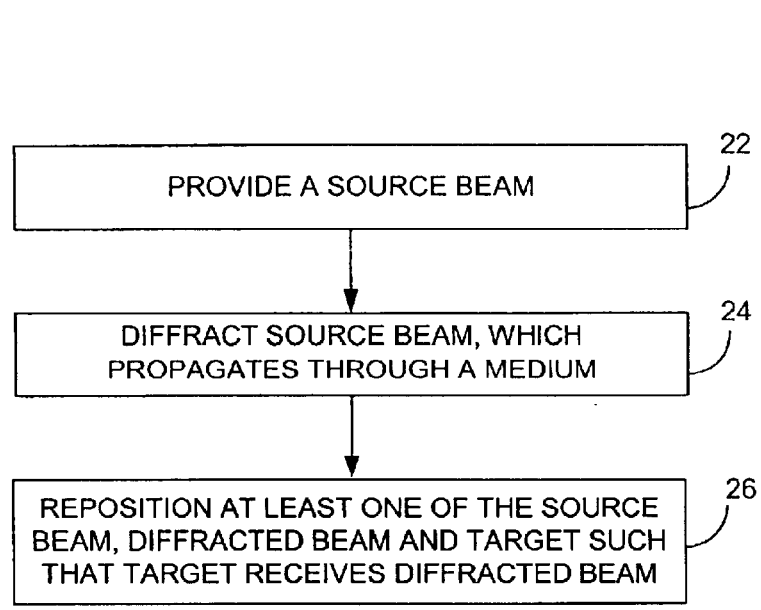
FIG. 3 is a flowchart depicting a method of operation of the embodiment of the optical system of FIG. 1.

As shown in FIG. 3, in block 22, a source beam of light is provided. The source beam is then diffracted, as indicated in block 24, to produce a diffracted beam, which propagates through a medium to a target. The index of refraction of the medium through which the diffracted beam propagates is subject to change. In particular, the medium is subject to change in at least one of temperature, pressure and humidity so that the refractive index changes. As described before, this can cause the diffracted beam to drift from the target. In block 26, at least one of the source beam, the diffracted beam and the target is repositioned so that the target continues to receive the diffracted beam. Therefore, the diffracted beam preferably is always incident upon the target.

Repositioning of the optical source, diffracting component and/or target can be accomplished in various manners. By way of example, the optical source and/or the target can be moved along respective axes. More specifically, the optical source can be moved along an axis that is perpendicular to the source beam, and the target can be moved along an axis that is perpendicular to the diffracted beam. By way of further example, the angular displacement of the diffracting component can be altered with respect to the source beam and/or target.

In some embodiments, the source beam and the diffracted beam carry one or more information signals which need not be interrupted while compensating for changes in atmospheric conditions. That is, in response to a change in refractive index, information signals can continue to propagate through the optical system while the compensating systems adjust the respective optical sources, diffracting components and/or targets. This is in contrast to many conventional optical systems that use an independent calibration signal for accommodating such changes. More specifically, such a system typically discontinues propagation of the information signal in order to correct for a change in atmospheric conditions. After the information signal is discontinued, a calibration signal is propagated through the system for determining required adjustments. After adjustments have been made, the information signal is propagated once again.

Figure 4:
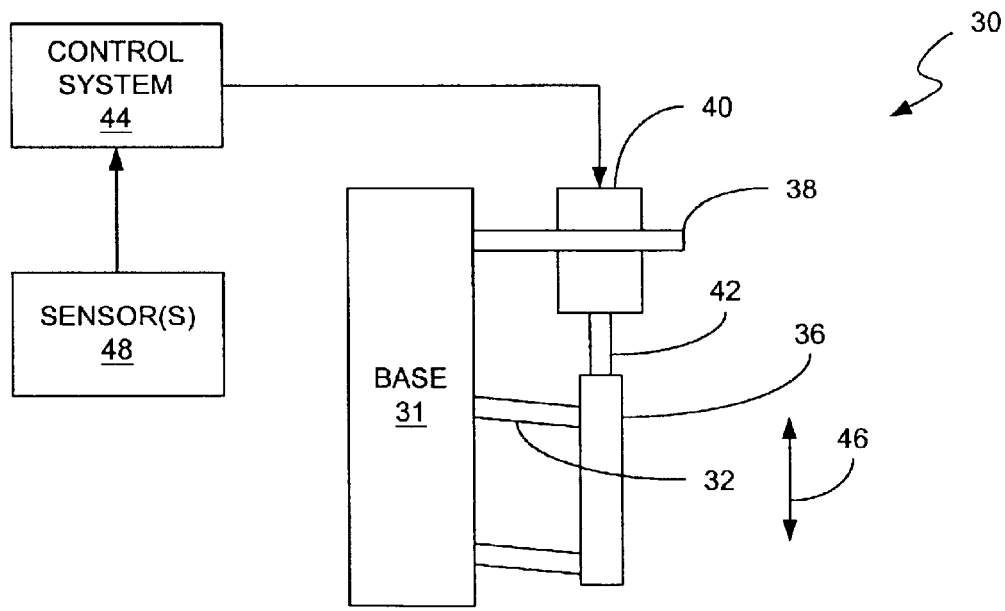
FIG. 4 is a schematic diagram of another embodiment of a compensating system in accordance with the invention.

FIG. 4 is a schematic diagram depicting an embodiment of a compensating system 30 in accordance with the invention. In FIG. 4, compensating system 30 includes a base 31 and support members 32 and 34 that attach a translation stage 36 to the base. More specifically, the support members are movable, e.g., hinged, so that the translation stage can be moved relative to the base. The translation stage is used to mount a target or an optical source (both of which are not shown in FIG. 4).

A support member 38 extends from the base and is used to mount an actuator 40. The actuator is attached to the translation stage by linkage 42 so that the actuator can reposition the translation stage and the associated optical source and/or target. In particular, translation stage 36 can be moved by the actuator in the directions indicated by arrow 46.

Control input for the actuator 40 is provided by a control system 44. The control system receives information from one or more sensors 48, which obtain information corresponding to the index of refraction of the medium through which the source beam and diffracted beam propagate. For instance, the refractive index of the medium can be sensed directly or parameters from which the refractive index can be determined are sensed. In particular, information corresponding to one or more of temperature, pressure, humidity and the index of refraction of the medium can be provided from the sensor(s) to the control system. In response to the information, the control system provides an input to the actuator for moving the translation stage. Thus, the optical source and/or the target is moved in response to a detected change in the index of refraction of the medium.

Control system 44 in accordance with the invention can be implemented in software (e.g., firmware), hardware, (e.g., analog and/or digital circuitry) or a combination thereof. When implemented in software, the control system can be an executable program that can be executed by a digital computer. When the control system is implemented in software, it should be noted that the control system can be stored on any computer-readable medium for use by or in connection with a computer-related system or method. A "computer-readable medium" store, communicate, propagate, or transport an executable program for use by or in connection with an instruction execution system, apparatus, or device.

The flowchart of FIG. 5 shows the functionality and/or operation of the embodiment of control system 44 of FIG. 4. As shown in FIG. 5, the functionality (or method) 44 may be construed as beginning at block 62, where information corresponding to at least one of temperature, pressure, humidity, and index of refraction of a medium through which optical signals propagate is received. In response to the information, the desired positions of one or more of an optical source, a diffracting component and a target are determined (block 64). In block 66, a control input is provided to reposition the optical source, the diffracting component and/or the target to the respective desired position.

Note, embodiments in accordance with the invention that rely on mechanical control also can be used. By way of example, FIG. 6 is a schematic diagram depicting another embodiment of a compensating system 70 in accordance with the invention. As shown in FIG. 6, compensating system 70 includes a frame 78 and a translation stage 80, which can be moved relative to the frame. Flexures 82, e.g., thin metal strips, each having a width substantially greater than their thickness are used to support the translation stage. The flexures enable the stage to move in a longitudinal direction but restrict movement of the stage in a direction perpendicular to a plane of the frame. Either the target or the optical source can be supported by the translation stage.

A bellows 84 is mounted on one side of the translation stage between the frame and the stage and is used to move the stage relative to the frame. Bellows 84 is sealed so that changes in atmospheric pressure surrounding the bellows cause the bellows to expand and contract. Thus, when the bellows expands in the X direction, a force is applied to translation stage 80 to push the stage in the +X direction, and when the bellows contracts, a force is applied to pull the stage in the −X direction. Note, the bellows 84 may be similar to those used in barometers, e.g., formed of metal.

The ability to compensate for changes is refractive index caused by atmospheric changes is highly desirable. By way of example, frequency detuning due to an altitude change from 0 to 1600 meters is significant for a spectrum analyzer used in an optical add-drop multiplexer (OADM) system. More information about an OADM system is provided in copending U.S. patent application Ser. No. 09/703,400, filed on Oct. 31, 2000, entitled "A Polarization-Independent, Configurable Optical Multiplexer," which is assigned to Agilent Technologies, and which is incorporated herein by reference.

The mathematical significance of a change in altitude in a typical OADM system can be shown with reference to the relationship between the frequency and wavelength of light in an optical medium, which is given by equation 1:

$$\frac{c}{n} = v\lambda_n \qquad (1)$$

where c is the speed of light in vacuum, n is the refractive index of the optical medium, v is the optical frequency, and $\lambda_n$ is the wavelength in the optical medium. The dependence of wavelength $\lambda_n$ on n and on v is given by the total derivative of equation (1), $$\delta\lambda = -\frac{c}{vn^2}\delta n - \frac{c}{nv^2}d\delta v \qquad (2)$$

which shows how an incremental wavelength change $\delta\lambda$ depends on an incremental index change $\delta n$ and an incremental frequency change $\delta v$.

With respect to an OADM system, an index change causes a particular wavelength of light propagating through the system in the form of a component of a diffracted beam to shift from its assigned target. The magnitude of this shift can be calculated by equating the two terms on the right hand side of equation (2), $$\delta v = \frac{v}{n}\delta n \qquad (3)$$

This is the fundamental relation between a change in refractive index $\delta n$ and OADM detuning $\delta v$.

The index of refraction of air at 1 atmosphere (atm) and 0 degrees Celsius (° C.) is approximately 1+2.9×10$^{-4}$. The (n−1) component is proportional to atmospheric pressure, which varies approximately exponentially with altitude with a 1/e altitude of about 7950 meters (m). Thus, at a 1600 m elevation, the exponential altitude dependence predicts a detuning of 15.5 GHz, which is a large fraction of the International Telecommunications Union (ITU) grid spacing of 50 GHz.

The foregoing description has been presented for purposes of illustration and description. It is not intended to be exhaustive or to limit the invention to the precise forms disclosed. Modifications and/or variations are possible in light of the above teachings. The embodiments discussed, however, were chosen and described to provide illustration of the principles of the invention and its practical application to thereby enable one of ordinary skill in the art to utilize the invention in various embodiments and with various modifications as are suited to the particular use contemplated.

By way of example, the bellows of the embodiment of FIG. 6 could be replaced with a sealed bladder that expands and contracts in response to changes in atmospheric pressure. All such modifications and/or variations are within the scope of the invention as determined by the appended claims when interpreted in accordance with the breadth to which they are fairly and legally entitled.

What is claimed is:

1. An optical system comprising:
   an optical source operative to propagate a source beam of light;
   a diffracting component optically coupled to the optical source, the diffracting component being operative to receive the source beam of light and produce a diffracted beam;
   a target located to receive the diffracted beam; and
   a compensating system operative to reposition at least one of the optical source, the diffracting component and the target in response to a detected change in refractive index of a medium through which the diffracted beam propagates such that the diffracted beam continues to be received by the target, and wherein the compensating system comprises:
   a translation stage upon which is disposed at least one of the optical source and the target; and
   a bellows mounted to the translation stage, the bellows being operative to move the translation stage by selectively expanding and contracting.

2. The optical system of claim 1, wherein:
the translation stage has a first end and a second opposing end, and the bellows is attached to the first end; and
the compensating system further comprises a first flexure mounted to the second end of the translation stage and supporting the translation stage as the translation stage is moved by the bellows.

3. The optical system of claim 1, wherein the translation stage moves along an axis perpendicular to the diffracted beam.

4. The optical system of claim 1, wherein the compensating system comprises a sensor operative to detect at least one of: temperature, pressure, humidity and a refractive index of the medium.

5. The optical system of claim 1, wherein:
the source beam and the diffracted beam carry an information signal; and
in response to a change in the index of refraction of the medium, the compensating system alters an angular displacement of the diffracting component relative to the target without interrupting the information signal carried by the diffracted beam.

6. The optical system of claim 1, further comprising: means for collimating the source beam.

7. The optical system of claim 1, further comprising:
a lens positioned between the optical source and the diffracting component, the lens being operative to collimate the source beam.

8. The optical system of claim 7, wherein the lens is also positioned between the diffracting component and the target.

9. The optical system of claim 1, wherein the compensating system further comprises:
a sensor operative to detect at least one parameter indicative of the refractive index of the medium.

10. The optical system of claim 1, wherein:
the compensating system further comprises an actuator operative to reposition at least one of the optical source, the diffracting component and the target.

11. The optical system of claim 1, wherein the optical source, diffracting component, target and compensating system form at least a portion of a spectrometer.

12. A method of compensating for a change in index of refraction of a medium, said method comprising:
providing a translation stage upon which is disposed at least one of an optical source and a target;
diffracting a source beam produced by the optical source, to produce a diffracted beam, the diffracted beam propagating through a medium to the target, the medium being subject to a change in index of refraction, the source beam being diffracted by a diffracting component to produce the diffracted beam; and
positioning the translation stage to compensate for the change in index of refraction of the medium such that the diffracted beam continues to be received by the target, wherein compensating for the change in index of refraction comprises angularly displacing the diffracting component.

13. The method of claim 12, wherein compensating for the change in index of refraction comprises detecting at least one of a temperature, a pressure and a humidity corresponding to the medium.

* * * * *